(12) United States Patent
Yin

(10) Patent No.: US 8,993,638 B2
(45) Date of Patent: Mar. 31, 2015

(54) BROMINATED NITROALKANOL COMPOSITIONS AND THEIR USE AS BIOCIDES

(75) Inventor: Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 737 days.

(21) Appl. No.: 12/796,694

(22) Filed: Jun. 9, 2010

(65) Prior Publication Data

US 2010/0317744 A1 Dec. 16, 2010

Related U.S. Application Data

(60) Provisional application No. 61/186,168, filed on Jun. 11, 2009.

(51) Int. Cl.
| | | |
|---|---|---|
| A01N 33/18 | (2006.01) | |
| A01N 33/24 | (2006.01) | |
| A61K 31/045 | (2006.01) | |
| C07C 205/00 | (2006.01) | |
| A01N 33/20 | (2006.01) | |

(52) U.S. Cl.
CPC ..................................... *A01N 33/20* (2013.01)
USPC .......................................... 514/727; 568/712

(58) Field of Classification Search
USPC .......................................... 514/727; 568/712
See application file for complete search history.

(56) References Cited

U.S. PATENT DOCUMENTS

| | | |
|---|---|---|
| 3,558,788 A | 1/1971 | Clark et al. |
| 2005/0277707 A1 | 12/2005 | Erickson |
| 2008/0004189 A1* | 1/2008 | Smith et al. .................... 507/129 |

FOREIGN PATENT DOCUMENTS

| | | |
|---|---|---|
| WO | 2009015088 A2 | 1/2009 |
| WO | 2009039004 A1 | 3/2009 |

OTHER PUBLICATIONS http://www.thefreedictionary.com/biocide.*
Linden et al., "The acute toxicity of 78 chemicals and pesticide formulations against 2 brackish water organisms, the bleak (alburnus-alburnus) and the harpacticoid nitocra-spinipes", Chemosphere, 1979, vol. 8, No. 11-12, pp. 843-852.
International Search Report and Written Opinion for PCT/US2010/037862 dated Sep. 3, 2010.

* cited by examiner

*Primary Examiner* — Sarah Pihonak
(74) *Attorney, Agent, or Firm* — Tifani M. Edwards

(57) ABSTRACT

Provided are biocidal compositions comprising: tris(hydroxymethyl)nitromethane; and a brominated nitroalkanol compound of formula I:

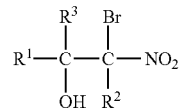

wherein $R^1$, $R^2$, and $R^3$ are as defined herein. The compositions are useful for controlling microorganisms in aqueous or water-containing systems.

9 Claims, No Drawings

BROMINATED NITROALKANOL COMPOSITIONS AND THEIR USE AS BIOCIDES

CROSS-REFERENCE TO RELATED APPLICATION(S)

This application claims benefit of priority from U.S. Provisional Patent Application No. 61/186,168, filed Jun. 11, 2009, which application is incorporated by reference herein in its entirety.

FIELD OF THE INVENTION

The invention relates to biocidal compositions and methods of their use for the control of microorganisms in aqueous and water-containing systems. The compositions comprise tris(hydroxymethyl)nitromethane and a brominated nitroalkanol compound.

BACKGROUND OF THE INVENTION

Protecting water-containing systems from microbial contamination is critical to the success of many industrial processes, especially oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Microbial contamination can occur anywhere throughout oil and gas operations including injection water, produced water, downhole, near wellbore areas, deaeration towers, transmission pipelines, source water for waterflooding and hydraulic fracturing such as pond water and holding tank water, oil and gas storage tanks, and functional water-based fluids such as drilling muds, completion or workover fluids, hydrotest fluids, stimulation fluids, packer fluids, and fracturing fluids.

Biocides are commonly used to disinfect and control the growth of microorganisms in aqueous systems including those found in oil and gas operations. However, not all biocides are effective against a wide range of microorganisms and/or temperatures, and some are incompatible with other chemical treatment additives. In addition, some biocides do not provide microbial control over long enough time periods. In oil and gas applications, the presence of $H_2S$ and elevated temperature present significant and unique challenges for biocide treatments.

It would be a significant advance in the art to provide thermally stable, fast acting, and long lasting biocides for oil and gas applications, including for downhole well treatment, where anaerobic SRB control is often critical.

BRIEF SUMMARY OF THE INVENTION

In one aspect, the invention provides biocidal compositions. The compositions are useful for controlling microbial growth in aqueous or water-containing systems, and are particularly suited for applications in the oil and natural gas industry. The compositions of the invention comprise tris(hydroxymethyl)nitromethane and a brominated nitroalkanol compound of formula I:

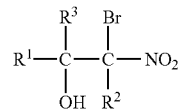

wherein $R^1$, $R^2$, and $R^3$ are as defined herein.

In a second aspect, the invention provides a method for controlling microorganisms in aqueous or water-containing systems. The method comprises treating the system with an effective amount of a biocidal composition as described herein.

DETAILED DESCRIPTION OF THE INVENTION

As noted above, the invention provides biocidal compositions and methods of using them in the control of microorganisms. The compositions comprise tris(hydroxymethyl)nitromethane and a brominated nitroalkanol compound. It has surprisingly been discovered that combinations of tris(hydroxymethyl)nitromethane and brominated nitroalkanol compound as described herein are synergistic when used for microorganism control in aqueous or water-containing media. That is, the combined materials result in improved biocidal properties than would otherwise be expected based on their individual performance at the particular use-concentration. The observed synergy permits reduced amounts of the materials to be used to achieve acceptable biocidal properties.

In addition to exhibiting synergy, the compositions of the invention are particularly effective at controlling anaerobic microorganisms. Further, the compositions are functional at both low and high temperature, and they also maintain their efficacy in systems that contain reducing agents, such as those that contain sulfide. As a result of these attributes, the compositions are well suited for use in the oil and natural gas industry where biocidal agents are needed that are capable of controlling microorganisms, including anaerobic microorganisms, over varying temperature ranges, and that continue to be effective when reducing agents, such as sulfides, are present.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism re-growth.

The composition of the invention comprises: tris(hydroxymethyl)nitromethane, and a brominated nitroalkanol compound of the formula I:

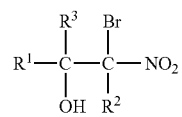

wherein $R^1$ is hydrogen, $C_1$-$C_{12}$ alkyl, or phenyl-$C_1$-$C_{12}$-alkyl-; $R^3$ is hydrogen, or $R^1$ and $R^3$, together with the carbon to which they are attached, form a $C_5$-$C_7$ cycloalkyl ring; and $R^2$ is hydrogen, methyl, ethyl, hydroxymethyl, or bromine.

Preferred brominated nitroalkanol compounds according to formula I include compounds in which $R^1$ is hydrogen or $C_2$-$C_{11}$ alkyl. Further preferred are compounds in which $R^1$ is methyl, ethyl, n-propyl, n-butyl, or n-hexyl. Also preferred are compounds in which $R^1$ and $R^3$, together with the carbon to which they are attached, form a cyclohexyl ring.

Preferred brominated nitroalkanol compounds according to formula I further include compounds in which $R^3$ is H.

Additionally preferred brominated nitroalkanol compounds according to formula I are compounds in which $R^2$ is hydroxymethyl.

Preferred compounds according to formula I include: 1-bromo-1-nitrobutan-2-ol; 2-bromo-2-nitro-1,3-propanediol; 1-bromo-1-nitropentan-2-ol; 2-bromo-2-nitrobutane-1,3-diol; 1-bromo-1-nitropropan-2-ol; 1,1-dibromo-3-methyl-1-nitrobutan-2-ol; 1-bromo-1-nitroheptan-2-ol; 1-bromo-1-nitrooctan-2-ol; 3-bromo-3-nitrobutan-2-ol; 1-(bromonitromethyl)cyclohexanol; 1,1-dibromo-1-nitropropan-2-ol; 1-bromo-1-nitrotridecan-2-ol; 2-bromo-2-nitroethanol; 1-bromo-1-nitrohexan-2-ol; 2-bromo-2-nitropentan-3-ol; 2-bromo-2-nitrobutan-1-ol; 1,1-dibromo-1-nitrobutan-2-ol; or mixtures of two or more thereof. Particularly preferred is 2-bromo-2-nitro-1,3-propanediol.

Brominated nitroalkanol compounds of formula I are commercially available and/or can be readily prepared by those skilled in the art using well known techniques (see e.g., U.S. Pat. No. 3,558,788, which is incorporated herein by reference). Tris(hydroxymethyl)nitromethane is commercially available.

The tris(hydroxymethyl)nitromethane to brominated nitroalkanol compound weight ratio in the compositions of the invention is preferably between 50:1 and 1:50, more preferably between 10:1 and 1:15, and more preferably between 5:1 and 1:7. In a further embodiment, the weight ratio is between 4:1 and 1:4. In another further embodiment, the weight ratio is between 2.8:1 and 1:1.

The compositions of the invention are useful for controlling microorganisms in aqueous or water-containing systems, such as those present in oil and natural gas applications. Examples of such systems include, but are not limited to, injection and produced water, source water for waterflooding and hydraulic fracturing such as pond water and holding tank water, functional fluids such as drilling muds, completion or workover fluids, hydrotest fluids, stimulation fluids, packer fluids, and fracturing fluids, oil and gas wells, separation, storage, and transportation systems, oil and gas pipelines, oil and gas vessels, or fuel.

The inventive compositions may also be used for controlling microorganisms in other industrial and water-containing systems such as cooling towers, heat exchangers, boiler systems, pulp and paper manufacture, other industrial process water, ballast water, wastewater treatment systems, reverse osmosis water processing, metalworking fluids, leather manufacture, paints and coatings, aqueous emulsions, latexes, adhesives, inks, pigment dispersions, personal care and household products, mineral slurries, caulks and adhesives, tape joint compounds, disinfectants, cleaners, textile fluids, or a system used therewith.

The compositions of the invention are functional over a wide temperature range. In some embodiments, therefore, the compositions are used in aqueous or water-containing systems at a temperature of 40° C. or greater. In further embodiments, the temperature of the aqueous or water containing system is 60° C. or greater, or is 80° C. or greater.

The compositions are also further effective when a reducing agent such as a source of sulfide ion is present in the aqueous or water-containing system.

The compositions are additionally effective when a reducing agent such as a source of sulfide ion is present in the aqueous or water-containing system and the temperature of the aqueous or water containing system is elevated. Preferably, the temperature of the aqueous or water containing system in this embodiment is 40° C. or greater, or 60° C. or greater, or 80° C. or greater.

In some embodiments, the microorganism being controlled with the compositions of the invention is anaerobic, such as SRB, and the aqueous system contains a reducing agent, such as sulfide. Under this embodiment, the tris(hydroxymethyl)nitromethane to brominated nitroalkanol compound weight ratio is preferably between about 4:1 to 1:4.

A person of ordinary skill in the art can readily determine, without undue experimentation, the concentration of the composition that should be used in any particular application. By way of illustration, a suitable actives concentration (total for both tris(hydroxymethyl)nitromethane and the brominated nitroalkanol compound) is typically between 1 and 2500 ppm, preferably between 5 and 1000 ppm, based on the total weight of the aqueous or water-containing system including the biocides. In some embodiments for oil and gas applications, it is preferred that active concentrations of the composition range from about 10 to about 300 ppm by weight, preferably about 30 to 100 ppm, for top side treatment, and from about 30 to about 500 ppm, preferably about 50 to about 250 ppm, for downhole treatment.

The components of the inventive compositions can be added to the aqueous or water-containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

The term "alkyl" as used herein, means a straight or branched chain hydrocarbon containing the indicated number of carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, n-octyl, and n-pentyl.

The term "cycloalkyl" as employed herein includes saturated and partially unsaturated cyclic hydrocarbon groups having 5 to 7 carbon atoms. Cyclohexyl is a preferred cycloalkyl groups.

The following examples are illustrative of the invention but are not intended to limit its scope. Unless otherwise indicated, ratios, percentages, parts, and the like used herein are by weight.

EXAMPLES

The synergy indexes reported in the following examples are calculated using the following equation:

$$\text{Synergy Index} = Ca/CA + Cb/CB$$

where Ca: Concentration of biocide A required to achieve a certain level or complete bacterial kill when used in combination;

CA: Concentration of biocide A required to achieve a certain level or complete bacterial kill when used alone;

Cb: Concentration of biocide B required to achieve a certain level or complete bacterial kill when used in combination; and CB: Concentration of biocide B required to achieve a certain level or complete bacterial kill when used alone.

A synergy index (SI) of 1 indicates additivity, a synergy index of less than 1 indicates synergy, and a synergy index greater than 1 indicates antagonism.

Various methods known to those skilled in the art can be used for evaluating biocidal efficacy. In the examples below, aliquots of the biocide-treated samples are removed at predetermined time points and the biocide concentration required to achieve a certain level or complete bacterial kill is determined by culture-based methods including serial dilution. In some examples, the method is based or adapted (e.g., for high temperature testing or for the presence of sulfide) from the methodology described in international patent publication WO 2009/039004, which is incorporated herein by reference.

Example 1

Synergistic Sffect of Tris(hydroxymethyl)nitromethane/2-bromo-2-nitro-1,3-propanediol Composition Against Sulfate Reducing Bacteria (SRB)

Inside an anaerobic chamber (Bactron IV), a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of Na2SO4, 43.92 mg of $Na_2CO_3$ in 1 L water) is contaminated with an oil field isolated anaerobic SRB consortium at final bacterial concentrations of $10^6$ to $10^7$ CFU/mL. The aliquots of this contaminated water are then treated with 2-bromo-2-nitro-1,3-propanediol (BNPD), tris (hydroxymethyl)nitromethane (TA), or the TA/BNPD combination of the invention, at different active concentration levels. After the mixtures are incubated at 40° C. for 24 hour, the biocidal efficacy is determined by minimum tested biocide concentration for bacteria kill in the aliquots (MBC). Table 1 summarizes the efficacy of the biocides, alone and in combination, and the Synergy Index at various concentrations.

TABLE 1

Biocidal efficacy and Synergy Index

| Ratio of BNPD to TA | MBC (active ppm) | | |
|---|---|---|---|
| (active w/w) | BNPD | TA | Synergy Index |
| 1:0* | 3.5 | 0.0 | |
| 7:1 | 3.5 | 0.5 | 1.00 |
| 2.9:1 | 3.5 | 1.2 | 1.02 |
| 1:1 | <2.7 | <2.7 | <0.83 |
| 1:2.8 | <2.7 | <7.6 | <0.97 |
| 1:8 | <2.7 | <21.6 | <1.35 |
| 0:1* | 0.0 | 36.5 | |

*comparative example

Example 2

Synergistic Effect of Tris(hydroxymethyl)nitromethane/2-bromo-2-nitro-1,3-propanediol Composition Against SRB for High Temperature and Sulfide-Rich Conditions Inside an anaerobic chamber (Bactron IV), biocides solutions are prepared in a deaerated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na_2SO_4$, 43.92 mg of $Na_2CO_3$ in 1 L water) and then challenged with $10^4$ to $10^5$ CFU/mL of an oilfield SRB consortium and 10 ppm sulfide ion. The mixtures are then incubated at 80° C. under anaerobic condition for 7 days. During the incubation, the solutions are challenged daily with $10^4$ to $10^5$ CFU/mL of the oilfield SRB consortium and 10 ppm sulfide. After incubation for 2 h the biocidal efficacy is evaluated against the field SRB consortium at 40° C. for 2 h. After incubation for 7 days the biocidal efficacy are evaluated again for 24 h. The biocidal efficacy is determined by the lowest testing biocide dosage concentration required to achieve a 3 log 10 or greater bacterial reduction, of both 2 hours and 7 days heat and SRB-sulfide exposure. Synergy Index is then calculated. Table 2 summarizes the biocides, alone and in combination, and the Synergy Index at various concentrations.

TABLE 2

Biocidal efficacy and Synergy Index

| Ratio of BNPD to TA | Dosage required for 3log10 bacterial reduction of both 2 h and 7 day heat and SRB-sulfide exposure (active ppm) | | |
|---|---|---|---|
| (active w/w) | BNPD | TA | Synergy Index |
| 1:0* | 180.0 | 0.0 | |
| 4:1 | 90.0 | 22.5 | 0.6 |
| 2:1 | 90.0 | 45.0 | 0.6 |
| 1:1 | 45.0 | 45.0 | 0.4 |
| 1:2 | 45.0 | 90.0 | 0.5 |
| 1:4 | 45.0 | 180.0 | 0.8 |
| 0:1* | 0.0 | 360.0 | |

*comparative example

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A synergistic composition comprising:
   tris (hydroxymethyl) nitromethane; and
   2-bromo-2-nitro-1,3-propanediol;
   wherein the weight ratio of tris (hydroxymethyl) nitromethane to 2 bromo-2-nitro-1,3-propanediol is between 4:1 and 1:4.

2. A composition according to claim 1 further comprising one or more additives selected from surfactants, ionic/nonionic polymers, scale and corrosion inhibitors, oxygen scavengers and additional biocides.

3. A method for controlling microorganisms in an aqueous or water-containing system, the method comprising treating the system with an effective amount of a composition according to claim 1.

4. A method according to claim 3 wherein the aqueous or water-containing system is used or is present in oil or gas production.

5. A method according to claim 4 wherein oil or gas production comprises injection and produced water, source water for waterflooding and hydraulic fracturing, pond water, holding tank water, functional fluids, drilling muds, completion and workover fluids, hydrotest fluids, stimulation fluids, packer fluids, fracturing fluids, oil and gas wells, separation, storage and transportation systems, oil and gas pipelines, oil and gas vessels, or fuel.

6. A method according to claim 3 wherein the aqueous or water-containing system is cooling towers, heat exchangers, boiler systems, pulp and paper manufacture, other industrial process water, ballast water, wastewater treatment systems, reverse osmosis water processing, metalworking fluids, leather manufacture, paints and coatings, aqueous emulsions, latexes, adhesives, inks, pigment dispersions, personal care and household products, mineral slurries, caulks and adhesives, tape joint compounds, disinfectants, cleaners, textile fluids, or a system used therewith.

7. A method according to one of claims 3-6 wherein the microorganisms are anaerobic bacteria.

8. A method according to one of claims 3-7 wherein the aqueous or water-containing system is at 40° C. or above.

9. A method according to one of claims 3-8 wherein the aqueous or water-containing system contains a reducing agent.

\* \* \* \* \*